(12) United States Patent
Chang

(10) Patent No.: US 6,183,200 B1
(45) Date of Patent: Feb. 6, 2001

(54) FAN DEVICE

(76) Inventor: Kwei-Tang Chang, No. 14, Lane 54, Luong Chuan St., Panchiao City, Taipei Hsien (TW)

( * ) Notice: Under 35 U.S.C. 154(b), the term of this patent shall be extended for 0 days.

(21) Appl. No.: 09/288,647

(22) Filed: Apr. 9, 1999

(51) Int. Cl.[7] .................................................. B63H 7/00
(52) U.S. Cl. ................................ 416/146 R; 416/170 R; 416/247 R; 416/246; 415/121.2; 96/63; 96/97
(58) Field of Search ..................... 415/121.2; 416/247 R, 416/146 R, 246, 170 R, 244 R; 96/97, 63; 422/124, 125, 305, 306; 417/423.1, 423.9, 423.14

(56) References Cited

U.S. PATENT DOCUMENTS

| | | | | |
|---|---|---|---|---|
| 2,720,013 | * | 10/1955 | Clarke | 416/146 R |
| 3,422,263 | * | 1/1969 | Asahina | 416/146 R |
| 4,515,538 | * | 5/1985 | Shih | 417/572 |
| 4,597,781 | * | 7/1986 | Spector | 55/126 |
| 5,259,726 | * | 11/1993 | Bacria | 415/119 |
| 5,820,660 | * | 10/1998 | Ko | 96/30 |

* cited by examiner

Primary Examiner—Edward K. Look
Assistant Examiner—Ninh Nguyen
(74) Attorney, Agent, or Firm—Rosenberg, Klein & Lee

(57) ABSTRACT

A fan device comprises a front fan cover, a blade device, a rear fan cover and a rotary front net. The front fan cover is installed with a first motor and a second motor therewithin. The blade means is installed behind the front fan cover and secured to the center of the shaft of the first motor for being driven to rotate by the first motor. The rear fan cover is installed behind the front fan cover and the blade device. The rear fan cover is combined with the front fan cover. The rotary front net has many lattices. The rotary front net is properly connected to the shaft center of the second motor and is driven to rotate by the second motor. The front fan cover is installed with a fragrant piece groove, a mosquito-repellent incense piece groove and an electric heat piece, and a fan leg frame is pivotally mounted to the rear fan cover. Thereby, the output wind can be diffuse uniformly and smoothly. Further, a fragrant piece groove and a mosquito-repellent incense piece groove are installed, thus the people will not feel uncomfortable.

9 Claims, 7 Drawing Sheets

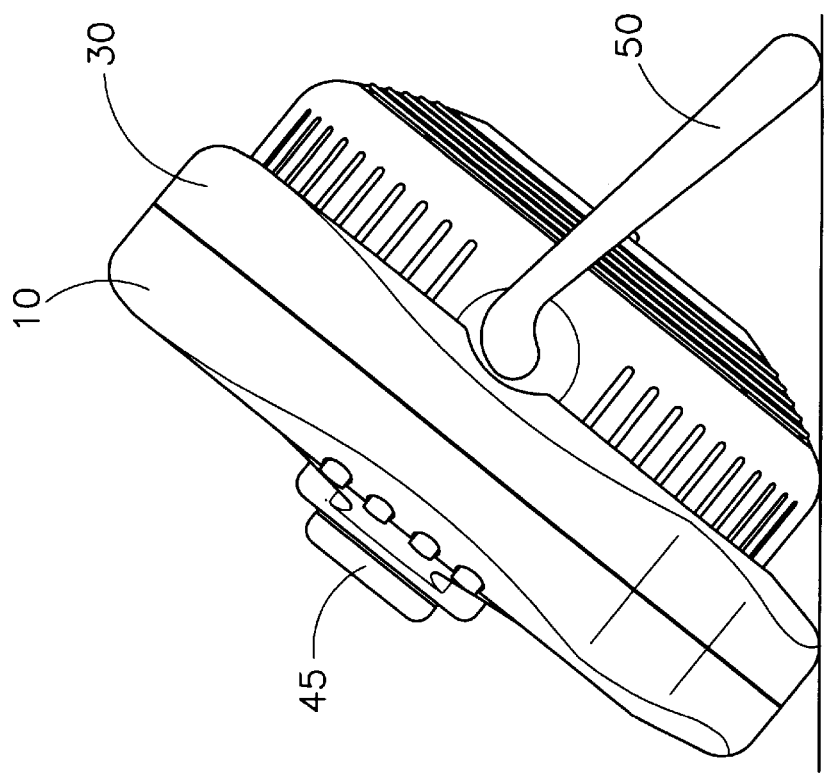
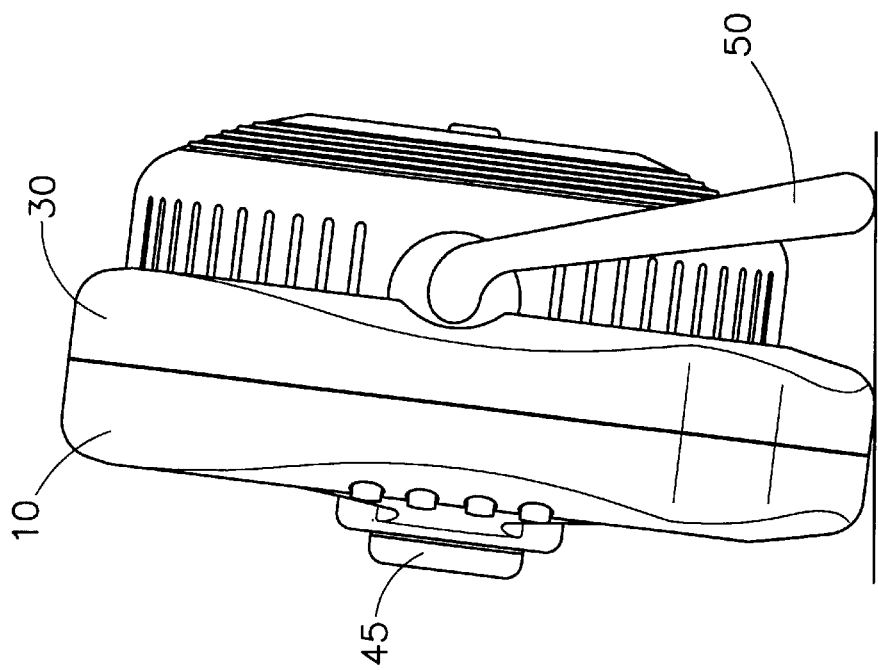

FAN DEVICE

BACKGROUND OF THE INVENTION

1. Field of the Invention

The present invention relates to a fan device designed with double front nets, wherein the output wind an be diffuse uniformly and smoothly, further a fragrant piece groove and a mosquito-repellent incense piece groove are installed, thus the people will feel comfortable.

2. Description of the Prior Art

As shown in FIG. 1, the prior art fan is a case fan, a blade device driven to rotated by a motor is installed therewithin. Another front fan cover 11a can be driven to rotate by another motor is installed in front of the blade 10a. The front fan cover 11a is formed as grids. In using the fan device, the wind will flow forward by the rotating blades 10a through the front fan cover 11a. Such kind of device may refer to Taiwan Patent No. 146452, etc.

However, in the aforesaid prior art fan structure, since it only designed with unique front fan cover 11a, the wind does not flow smoothly, thus people will feel uneasy. Moreover, in the prior art, the blades 10a and the front fan cover 11a are pivotally installed within an outer frame 12a so as to adjust the blades 10a to a different elevation angle. When the blades 10a and the front fan cover 11a are adjusted to an angle to output wind upwards, the wind will be hindered by the upper portion 13a of the outer frame 12a. Thus, the wind can not flow successfully. Moreover, the prior art fan device only has the function of outputting wind but has not contain the functions of fragrant device and the mosquito-repellent incense device.

SUMMARY OF THE INVENTION

Accordingly, the object of the present invention is to provide a fan device which has a special designed rotary front net with many lattices. By this net design, the output wind can be diffuse uniformly and smoothly.

Another object of the present invention is to provide a fan device installed with a negative ion generator for adhering with dust so as to clean air.

Another object of the present invention is to provide a fan device installed with a fragrant piece groove and a mosquito-repellent incense piece groove for being inserted by fragrant pieces and mosquito-repellent incense pieces, and an electric heating piece is adjacent to the grooves. The fragrant pieces or mosquito-repellent incense pieces will emit fragrant odor to flow outwards with the wind, so that the fan has the functions of a fragrant device and a mosquito-repellent incense device.

A further object of the present invention is to provide a fan device design with an adjustable fan leg frame for adjusting the fan device to different elevation angle. However, the fan does not designed with an outer frame, therefore, irrespective of the fan device being adjusted to any orientation, it will not be hindered by the outer frame. As a result, the wind can be outputted successfully.

The present invention will be better understood and its numerous objects and advantages will become apparent to those skilled in the art by referencing to the following drawings in which:

BRIEF DESCRIPTION OF THE DRAWINGS

FIG. 4 is a side view of the present invention.

FIG. 5 is a side view showing that the present invention is adjusted to different elevation angles.

DETAILED DESCRIPTION OF THE PREFERRED EMBODIMENT

Figure 1:
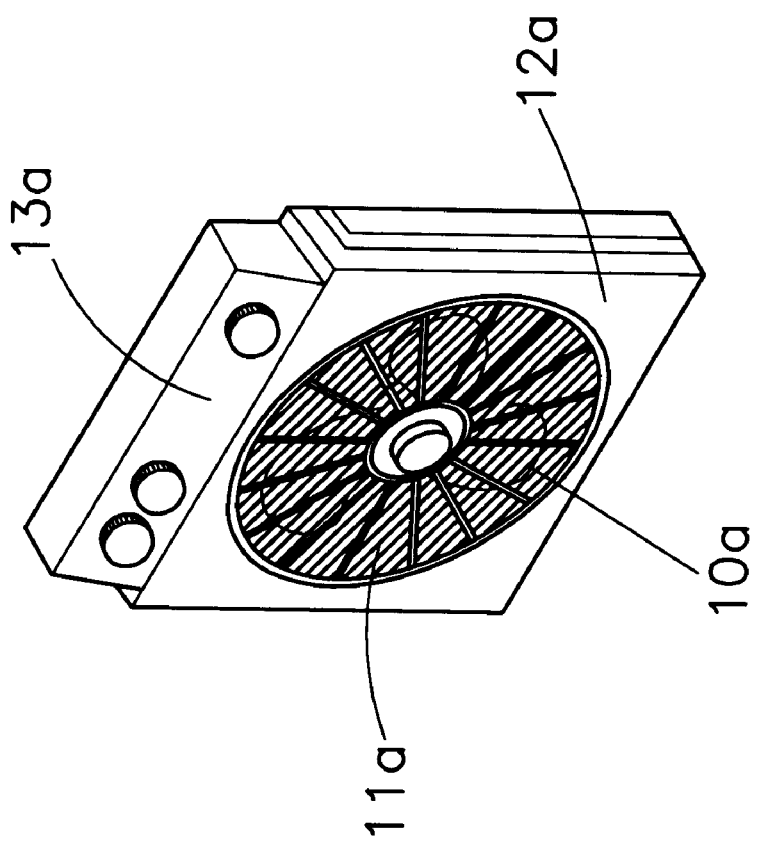
FIG. 1 is a perspective view of a prior fan device.
Figure 2:
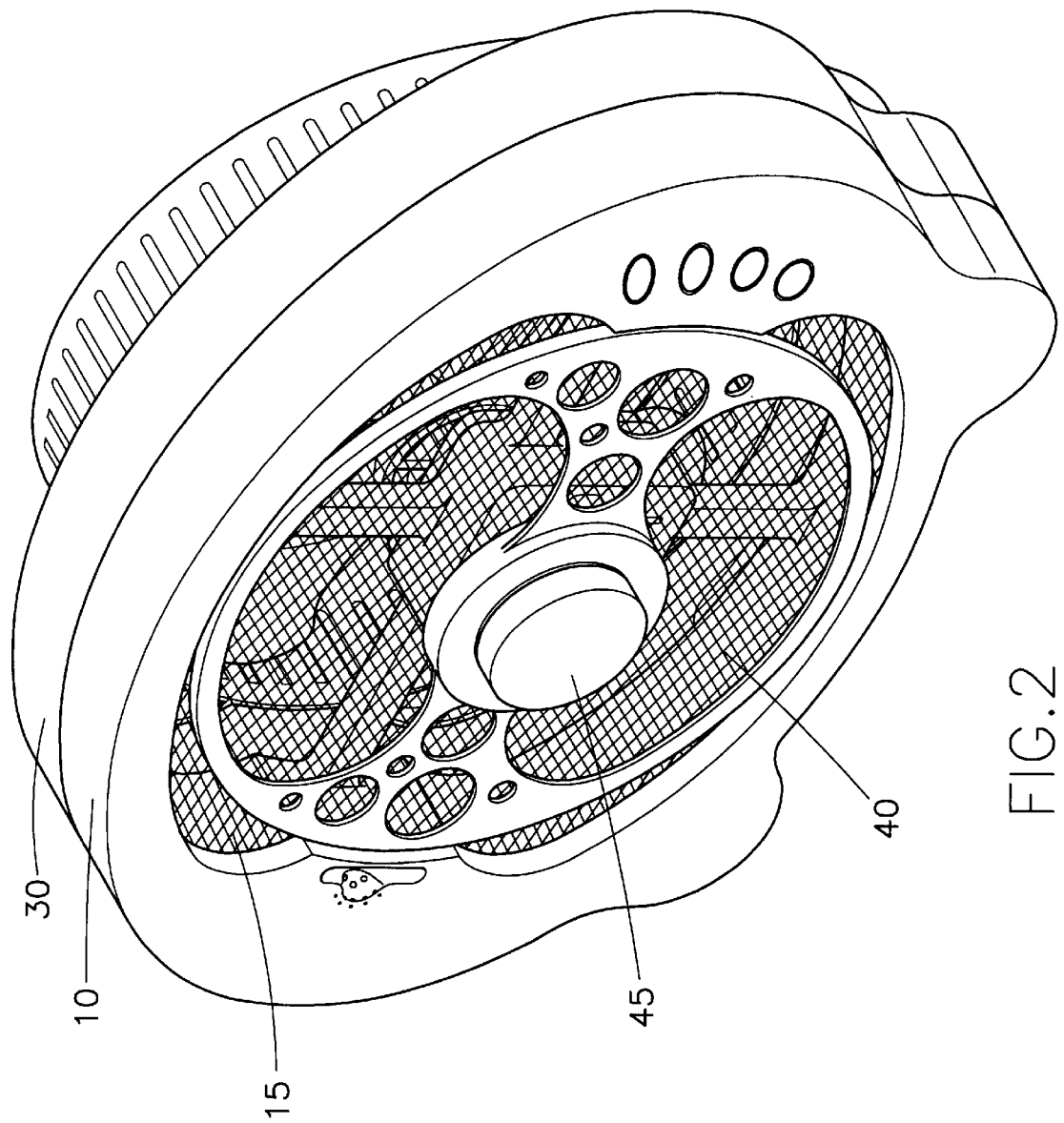
FIG. 2 is a perspective view of the present invention.
Figure 3A:
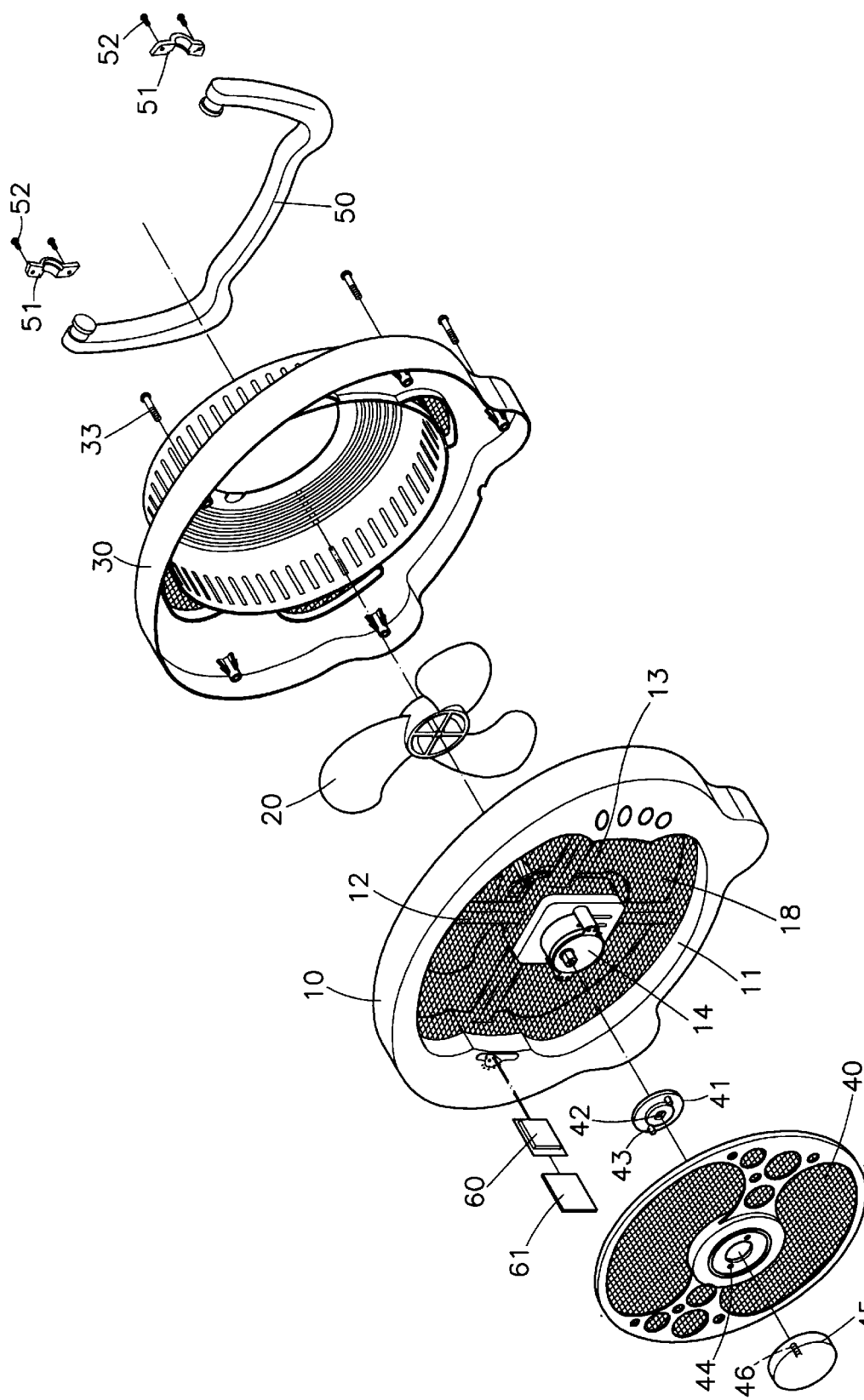
FIG. 3A is an exploded perspective view of the present invention.
Figure 3B:
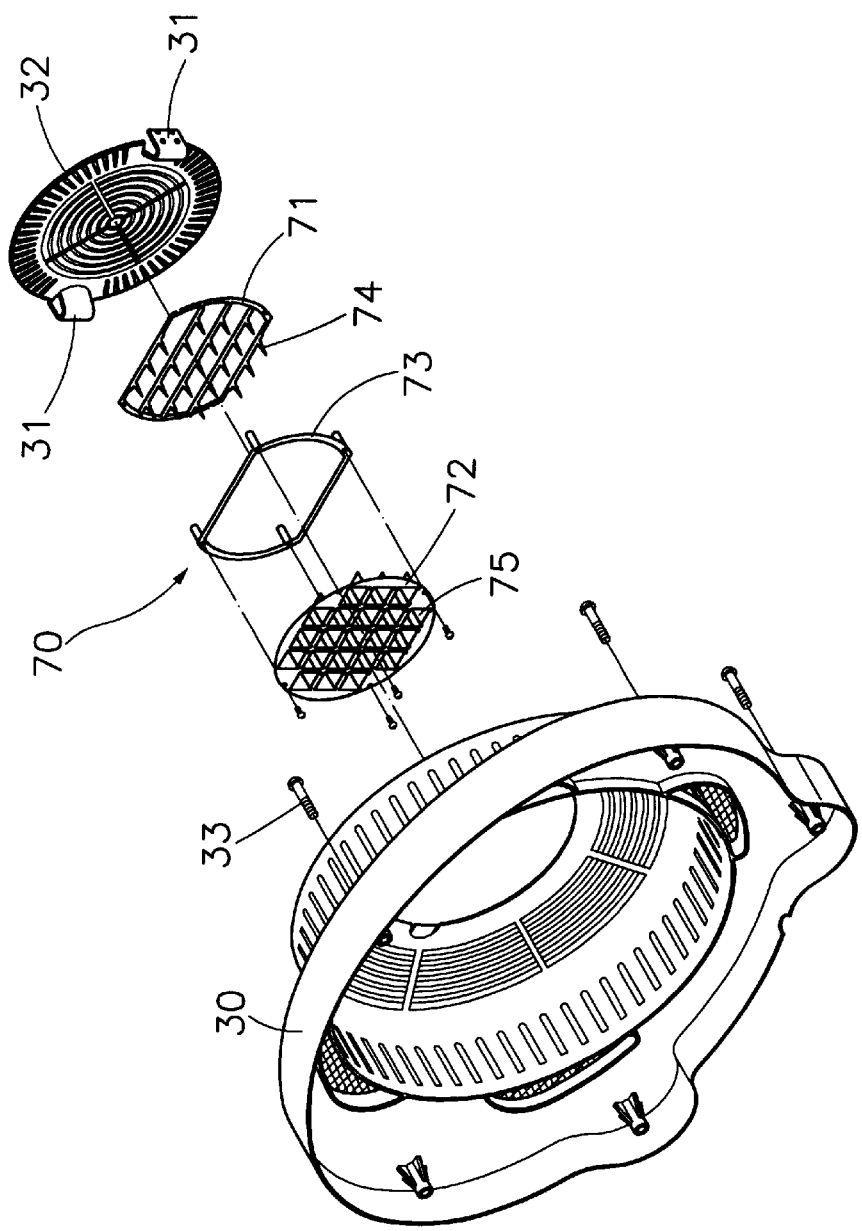
FIG. 3B is another exploded perspective view of the present invention.
Figure 6:
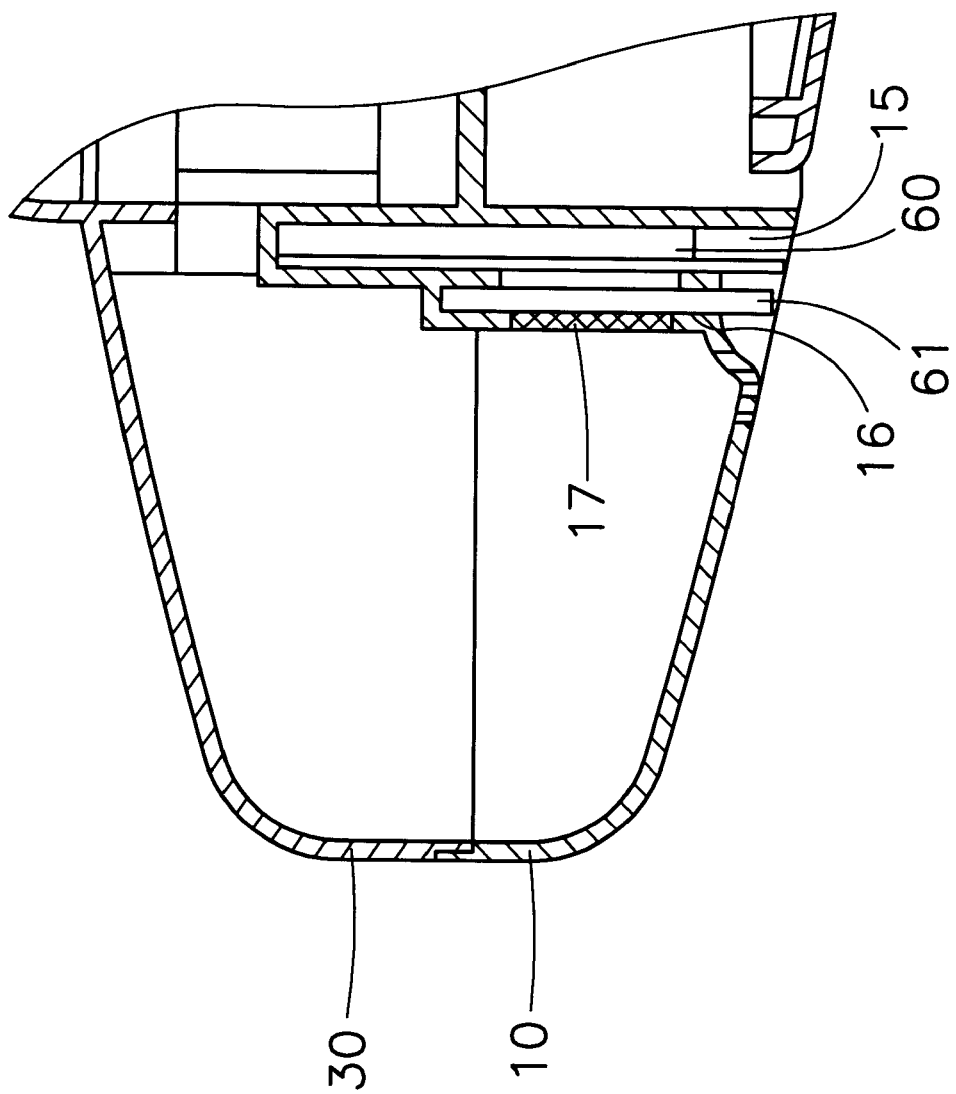
FIG. 6 is a cross sectional view of the fragrant piece groove and the mosquito-repellent incense piece groove of the present invention.

As shown in FIGS. 2, 3A and 3B, the fan device of the present invention is disclosed. The fan device of the present invention includes a front fan cover 10, a blade device 20, a rear fan cover 30, a rotary front net 40 and a leg frame 50. The front fan cover 10 is a hollow body. The through hole 11 is formed therewithin. Four supporting frames 12 fixing a first motor 13 are formed on the center of the through hole 11. A second motor 14 is further installed on the front side of the first motor 13. A fragrant piece groove 15 and a mosquito-repellent incense piece groove 16 can be installed on the front fan cover 10 (as that shown in FIG. 6). An electric heating piece 17 adjacent to the fragrant piece groove 15 and the mosquito-repellent incense piece groove 16 are securely installed on the front fan cover 10. The fragrant piece groove 15 and the mosquito-repellent incense piece groove 16 can be inserted with respective a fragrant piece 60 and a mosquito-repellent incense piece 16. The through hole 11 of the front fan cover 10 is installed with a fixing front net 18 which is formed by a lattice and is formed between the first motor 13 and the second motor 14.

The blade device 20 is installed behind the front fan cover 10 and is properly secured to the shaft center of the first motor 13 by screwing and other ways. The first motor 13 can be driven by a proper circuit (not shown) for driving the blade device 20 to rotate and output wind forward.

The rear fan cover 30 is installed on the rear side of the front fan cover 10 and the blade device 20. The rear side of the rear fan cover 30 is installed with a fixing rear net 32 which are buckled to the rear fan cover 30 by hooks 31 on the two sides thereof. The rear fan cover 30 is locked integrally to the front fan cover 10 by a plurality of screws 33.

The rotary front net 40 is installed within the through hole 11 of the front fan cover 10 and is in front of the fixing front net 18. The rotary front net 40 has a plurality of lattices. A rotary disk 41 is installed between the rotary front net 40 and the second motor 14. The rotary disk 41 is embedded in the shaft center of the second motor 14 by an embedding hole 42 and has two pins 43 in the front thereof. Two respective pin holes 44 are formed on the rotary front net 40. The rotary front net 40 matches with the two pins 43 through the two pin holes 44. The second motor 14 can be driven by a proper circuit (not shown) for driving the rotary disk 41 and the rotary front net 40 to rotate synchronously. A cover hood 45 is installed in front of the rotary front net 40 and a screw 46 is securely installed to the rear side of the cover hood 45. It is screwedly connected to the front end of the second motor 14 by screws 46 for preventing releasing of the rotary disk 41 and the rotary front net 40. When the cover hood 45 looses, the rotary front net 40 can be easily detached and attached.

Figure 7:
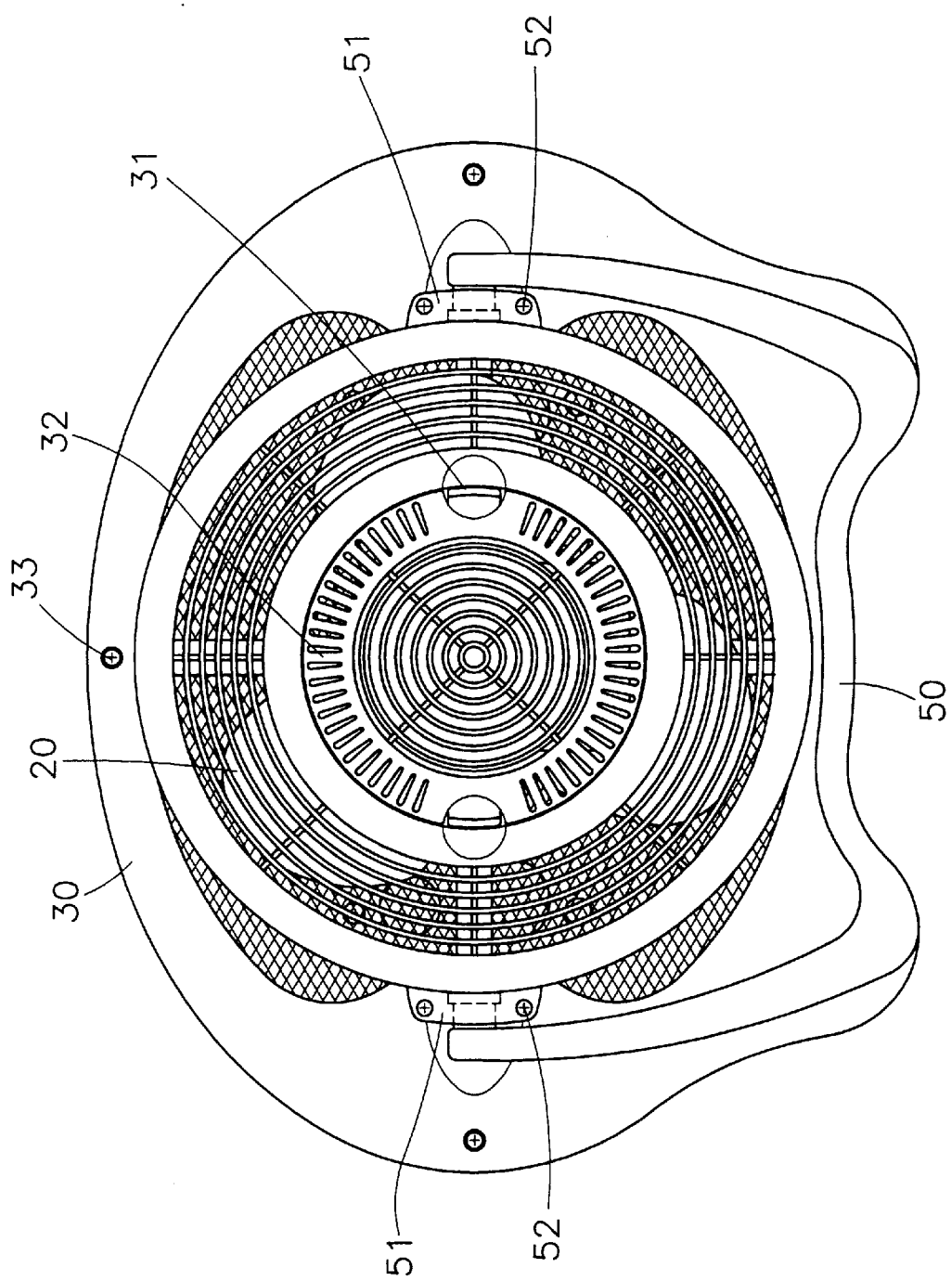
FIG. 7 is a rear view showing that the pivotal structure of the fan leg frame of the present invention.

The fan leg frame 50 is installed on rear side of the rear fan cover 30 and has a "U" shape. Each of the two ends of the fan leg frame 50 matches with a respective pivotal seat 51 which are screwedly locked to rear side of the rear fan cover 30 by screws 52 (as shown in FIG. 7). As the fixing button is released, the fan leg frame 50 can be adjusted (as shown in FIG. 5) for the purpose of adjusting different elevation angle of the fan.

Moreover, in the present invention, a negative ion generator 60 can be further installed within the rear fan cover 30, which includes an anode pin plate 71, a cathode plate 72 and a frame 73. The anode pin plate 70, cathode plate 72 and frame 73 are fixed within the fan rear cover 30. A plurality of discharging pins 74 are installed on the anode pin plate 71. A plurality of through holes 75 are installed on the cathode plate 72. The discharging pins 74 of the anode pin plate 71 are correspondent to the exact centers of the through holes 75 of the cathode plate 72. A high direct current voltage is applied between the anode pin plate 71 and the cathode plate 72. Since the negative ion released from the discharging pins 74 to the cathode plate 72 will adhere to the dust particles pass through the two electrodes so that the particle is negative ionized so as to finally adhere to the positive anode pin plate 71. Thus the effect of cleaning air is achieved.

In using the fan device of the present invention, the rotary fan 20 may draw air to flow forward through the fixing front net 18 and the rotary front net 40. The present invention is designed with a rotary front net 40 with lattices, the output wind can be diffuse uniformly and smoothly, thus the people will not feel uncomfortable. The present invention is designed with a fixing front net 18 and a rotary front net 40, by this double nets design, the output wind can be diffuse uniformly and smoothly. Moreover, the present invention is design with an adjustable fan leg frame 50 for adjusting the fan device to a different elevation angle. However, the fan does not designed with an outer frame, therefore, no matter the fan device is adjusted to any orientation, it will not be hindered by the outer frame. As a result, the wind can be outputted successfully. Alternatively, the fragrant piece groove 15 and the mosquito-repellent incense piece groove 16 are installed on the front fan cover 10 for being inserted by fragrant pieces 60 and mosquito-repellent incense pieces 61, respectively. When the electric heating piece 17 is conducted and heated, the fragrant pieces 60 or mosquito-repellent incense pieces 61 will emit a fragrant odor and flow outward with the wind, so that the fan has the functions of a fragrant device and a mosquito-repellent incense device.

Although the present invention has been described using specified embodiment, the examples are meant to be illustrative and not restrictive. It is clear that many other variations would be possible without departing from the basic approach, demonstrated in the present invention. Therefore, all such variations are intended to be embraced within the scope of the invention as defined in the appended claims.

What is claimed is:

1. A fan device comprising:
    a front fan cover installed with a first motor and a second motor, the second motor being positioned in front of the first motor, the front fan cover being installed with a fixing front net disposed between the first and second motors, the fixing front net being formed by a lattice;
    a blade device installed behind the front fan cover and secured to a shaft of the first motor for being driven to rotate by the first motor;
    a rear fan cover installed behind the front fan cover and the blade device, the rear fan cover being combined with the front fan cover;
    a negative ion generator being installed within the rear fan cover; and,
    a rotary front net with lattices, the rotary front net being connected to a shaft of the second motor and being driven to rotate by the second motor.

2. The fan device as claimed in claim 1, wherein a fixing rear net is combined to a rear side of the rear fan cover.

3. The fan device as claimed in claim 1, wherein a rotary disk is installed between the rotary front net and the second motor, the rotary disk being embedded on the shaft of the second motor, a front side of the rotary disk having a plurality of pins installed thereon, the rotary front net having a plurality of pin holes in correspondence with the pins on the front of the rotary disk, a cover hood is formed in front of the rotary front net, a rear side of the cover hood is securely installed with a screw to a front end of the second motor.

4. The fan device as claimed in claim 1, wherein a fan leg frame is pivotally installed on a rear side of the rear fan cover.

5. The fan device as claimed in claim 4, wherein each of two ends of the fan leg frame is respectively installed to a pivotal seat, the two pivotal seats being respectively fixed to the rear side of the rear fan cover by screws.

6. The fan device as claimed in claim 1, wherein the negative ion generator is installed with an anode pin plate, a cathode plate, and a frame, the anode pin plate is installed with a plurality of discharging pins, the cathode plate is installed with a plurality of through holes, the plurality of discharging pins of the anode pin plate being in respective correspondence with the plurality of through holes of the cathode plate.

7. A fan device comprising:
    a front fan cover installed with a first motor and a second motor therewithin, the second motor being positioned in front of the first motor, a fixing front net being installed between the first motor and the second motor, at least one groove and an electric heating piece being installed in the front fan cover, the electric heating piece being adjacent to the groove;
    a blade device installed behind the front fan cover and secured to a shaft of the first motor for being driven to rotate by the first motor;
    a rear fan cover installed behind the front fan cover and the blade device, the rear fan cover being combined with the front fan cover; and
    a rotary front net installed in front of the fixing front net, the rotary front net being connected to a shaft of the second motor and being driven to rotate by the second motor.

8. The fan device as claimed in claim 7, further comprising at least one fragrant piece inserted into the at least one groove in the front fan cover.

9. The fan device as claimed in claim 7, further comprising at least one mosquito-repellent piece inserted into the at least one groove in the front fan cover.

* * * * *